(12) United States Patent
Tomita et al.

(10) Patent No.: US 11,464,682 B2
(45) Date of Patent: Oct. 11, 2022

(54) ABSORBENT ARTICLE

(71) Applicant: KAO CORPORATION, Tokyo (JP)

(72) Inventors: Mina Tomita, Utsunomiya (JP);
Akihito Akutagawa, Saitama (JP);
Takeshi Suzuki, Sano (JP); Ayuka Minamizaki, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 894 days.

(21) Appl. No.: 16/329,923

(22) PCT Filed: Oct. 27, 2017

(86) PCT No.: PCT/JP2017/038924
§ 371 (c)(1),
(2) Date: Mar. 1, 2019

(87) PCT Pub. No.: WO2018/100945
PCT Pub. Date: Jun. 7, 2018

(65) Prior Publication Data
US 2019/0201254 A1 Jul. 4, 2019

(30) Foreign Application Priority Data

Nov. 30, 2016 (JP) .............................. JP2016-233641

(51) Int. Cl.
*A61F 13/15* (2006.01)
*A61F 13/511* (2006.01)
(Continued)

(52) U.S. Cl.
CPC ...... *A61F 13/51104* (2013.01); *A61F 13/514* (2013.01); *A61F 13/5116* (2013.01);
(Continued)

(58) Field of Classification Search
CPC ............ A61F 13/51104; A61F 13/5116; A61F 13/514; A61F 2013/15991;
(Continued)

(56) References Cited

U.S. PATENT DOCUMENTS 7,303,808 B2 12/2007 Taneichi et al.
2001/0026858 A1 10/2001 Takai et al.
(Continued)

FOREIGN PATENT DOCUMENTS

CA 2 340 904 A1 9/2001
CN 101310696 A 11/2008
(Continued)

OTHER PUBLICATIONS

International Search Report, issued in PCT/JP2017/038924, PCT/ISA/210, dated Dec. 12, 2017.

*Primary Examiner* — Jacqueline F Stephens
(74) *Attorney, Agent, or Firm* — Birch, Stewart, Kolasch & Birch, LLP

(57) ABSTRACT

An absorbent article includes a topsheet comprising a composite sheet. In the composite sheet, projections that protrude toward the skin of the wearer are formed by a first sheet protruding in a direction away from a second sheet at portions other than bonding portions. A plurality of first oblique bonding portion rows and a plurality of second oblique bonding portion rows are formed, and a long bonding portion elongated in a longitudinal direction is formed at each intersection of the first oblique bonding portion rows and the second oblique bonding portion rows. Laterally long projections elongated in a width direction are formed in a dispersed manner in the longitudinal direction and the width direction. Each laterally long projection is surrounded by two first oblique bonding portion rows and two second oblique bonding portion rows, and the long bonding portion is formed between adjacent laterally long projections in the width direction.

20 Claims, 7 Drawing Sheets

(51) Int. Cl.
    *A61F 13/514*    (2006.01)
    *A61F 13/53*    (2006.01)
(52) U.S. Cl.
    CPC .... *A61F 13/53* (2013.01); *A61F 2013/15991* (2013.01); *A61F 2013/51139* (2013.01); *A61F 2013/51165* (2013.01); *A61F 2013/530583* (2013.01)
(58) Field of Classification Search
    CPC .... A61F 2013/51139; A61F 2013/5116; A61F 2013/530583
    See application file for complete search history.

(56) References Cited

U.S. PATENT DOCUMENTS

| | | |
|---|---|---|
| 2002/0061390 A1 | 5/2002 | Kobayashi et al. |
| 2003/0068467 A1 | 4/2003 | Takai et al. |
| 2015/0238370 A1 | 8/2015 | Uda et al. |
| 2017/0014280 A1 | 1/2017 | Moritani |

FOREIGN PATENT DOCUMENTS

| | | |
|---|---|---|
| CN | 104939980 A | 9/2015 |
| CN | 104661629 B | 8/2016 |
| CN | 205411476 U | 8/2016 |
| DE | 69226651 T3 | 4/2004 |
| JP | 2009-136349 A | 6/2009 |
| JP | 5053815 B2 | 10/2012 |
| JP | 5211035 B2 | 6/2013 |
| JP | 2016-116579 A | 6/2016 |
| JP | 2016-116582 A | 6/2016 |
| JP | 2016-116584 A | 6/2016 |
| JP | 2016-116847 A | 6/2016 |
| RU | 2 091 081 C1 | 9/1997 |
| RU | 2 362 530 C2 | 7/2009 |
| TW | 570874 B | 1/2004 |
| WO | WO 91/15368 A1 | 10/1991 |
| WO | WO 93/11726 A1 | 6/1993 |
| WO | WO 2013-077074 A1 | 5/2013 |
| WO | WO 2015/146452 A1 | 10/2015 |
| WO | WO 2016/098848 A1 | 6/2016 |

[Fig. 1]
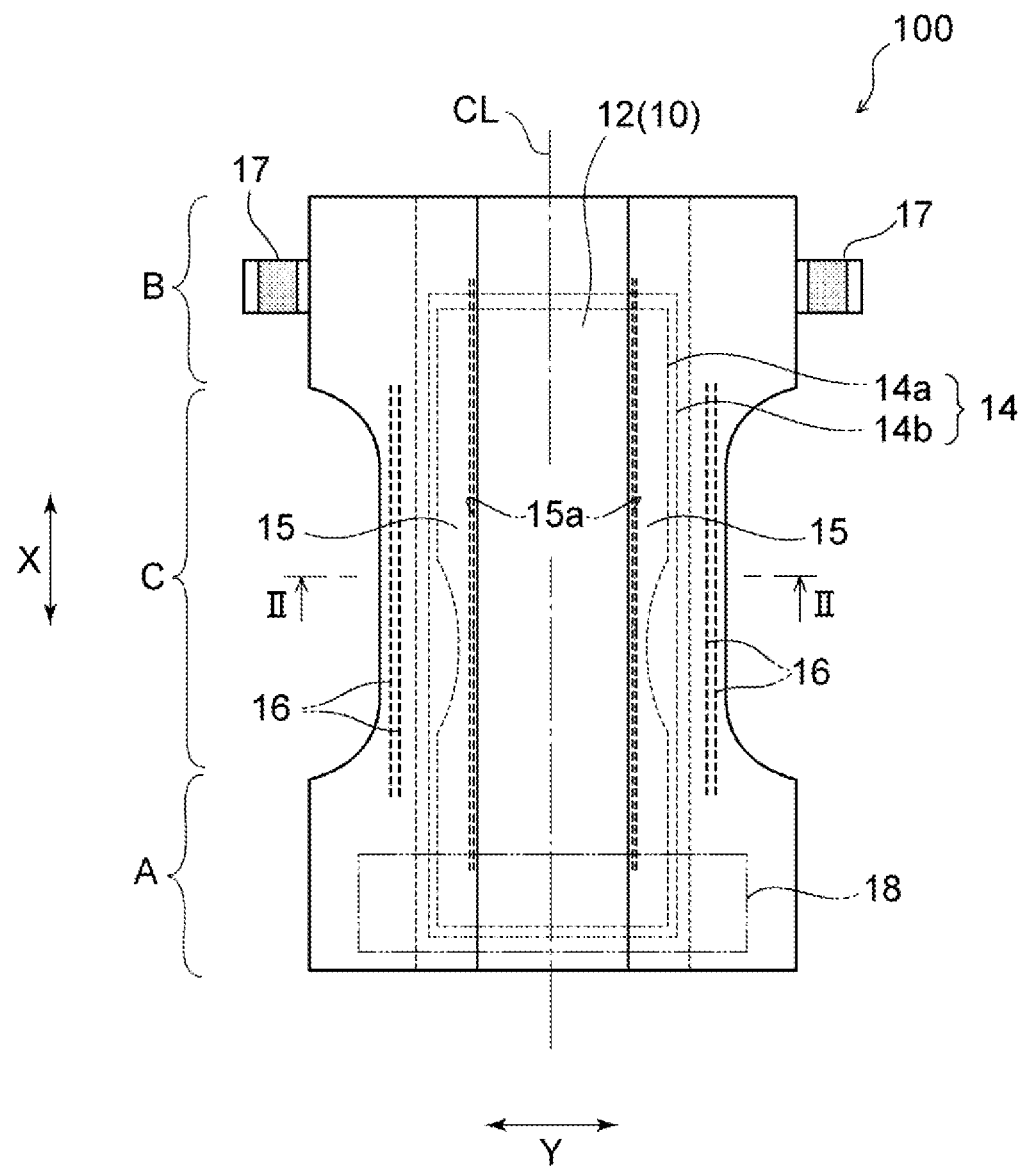

[Fig. 2]
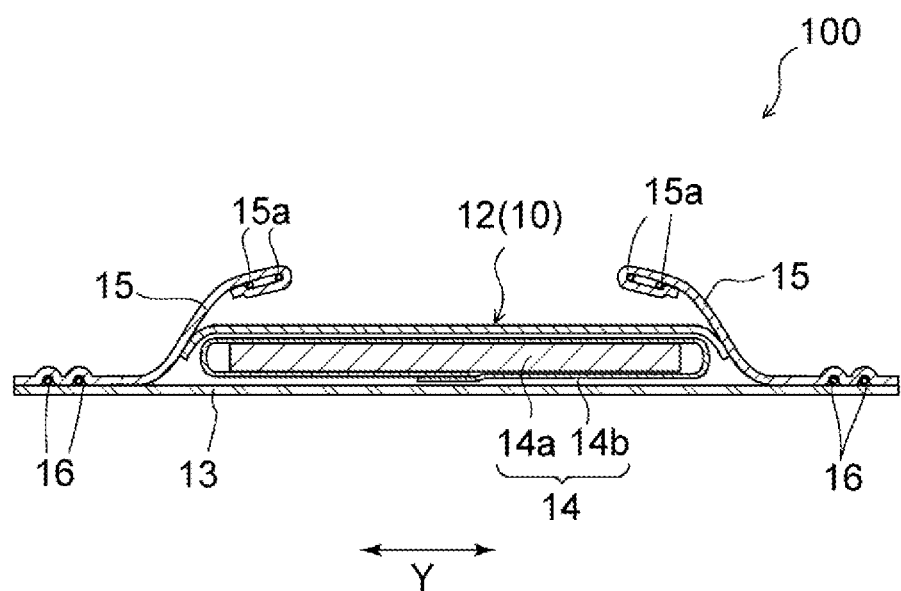

[Fig. 3]
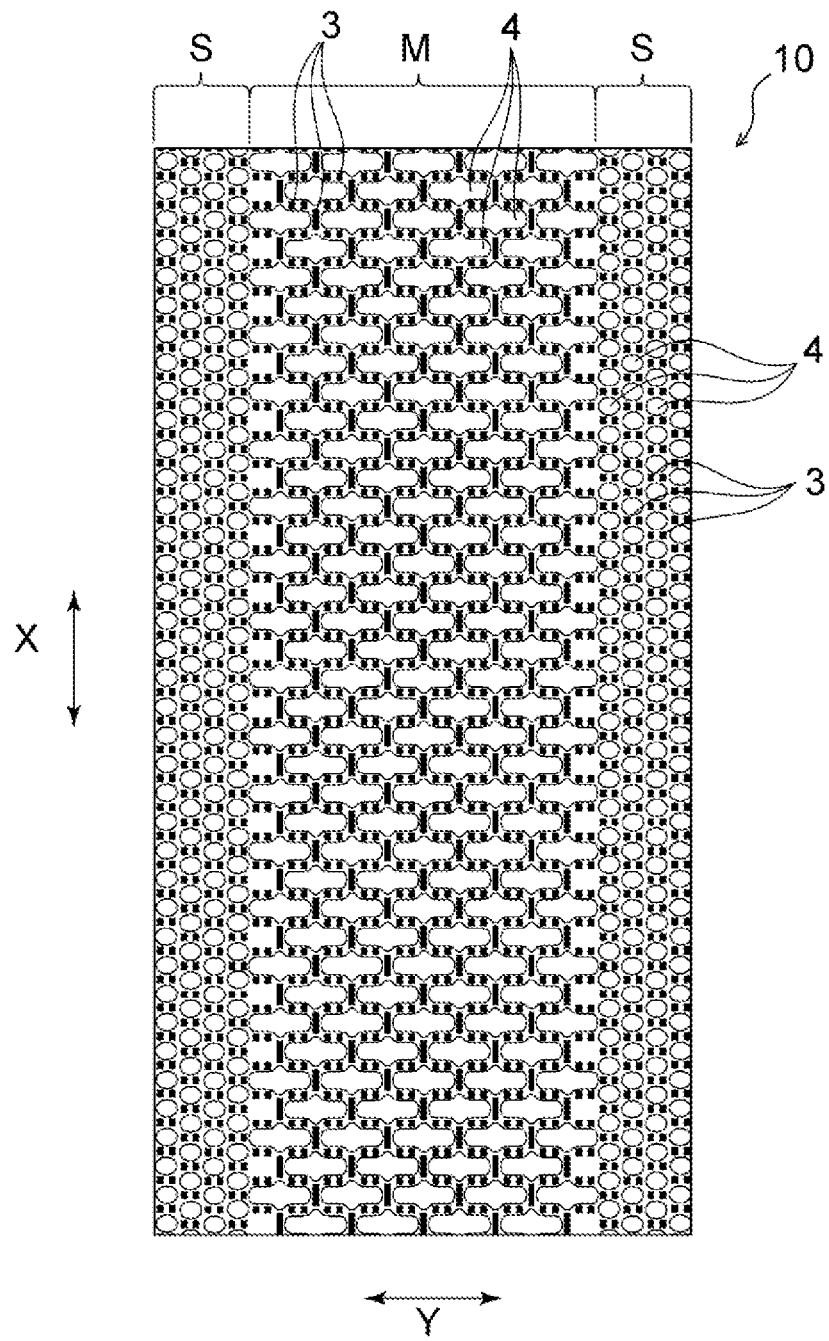

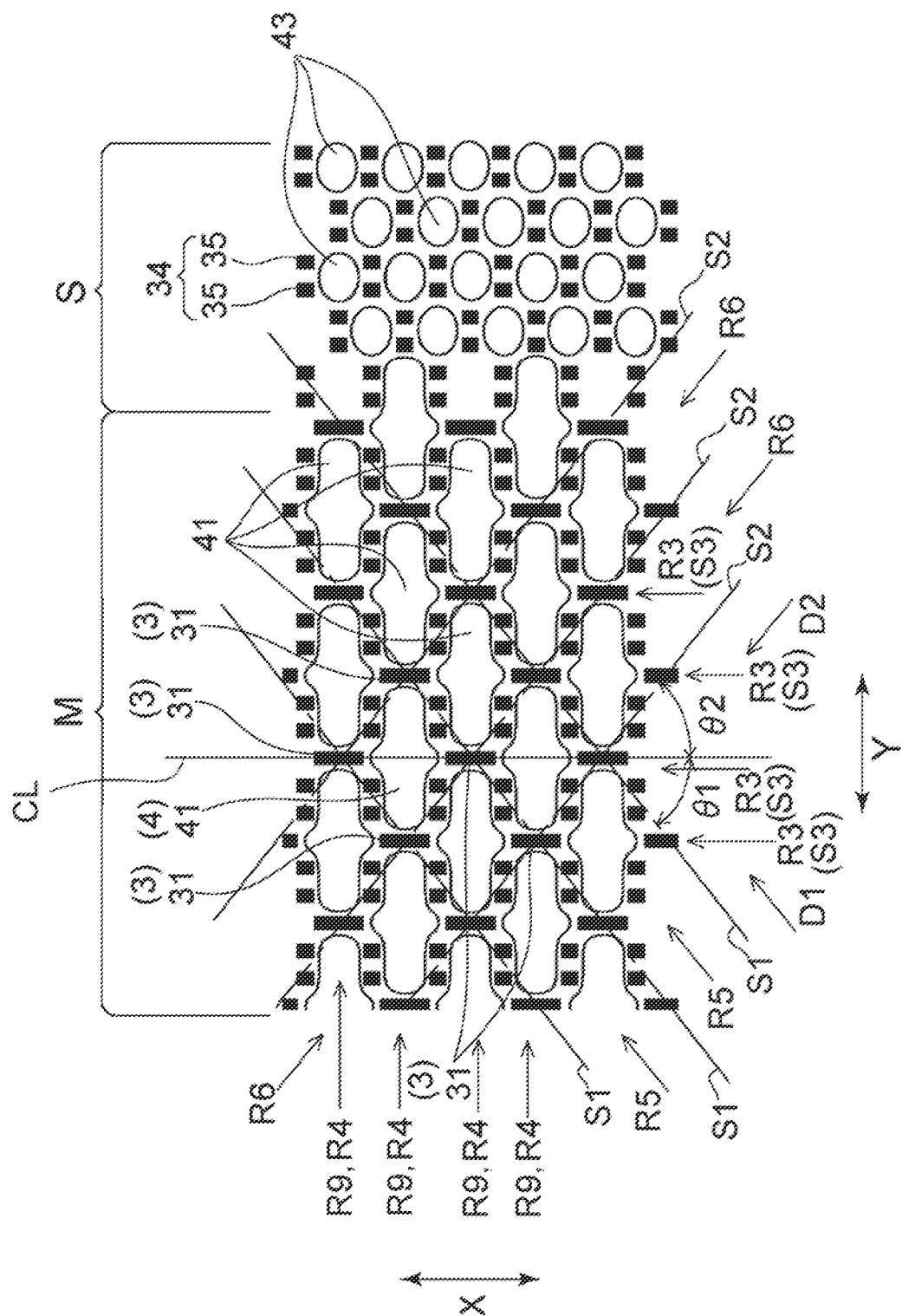
[Fig. 4]

[Fig. 5]
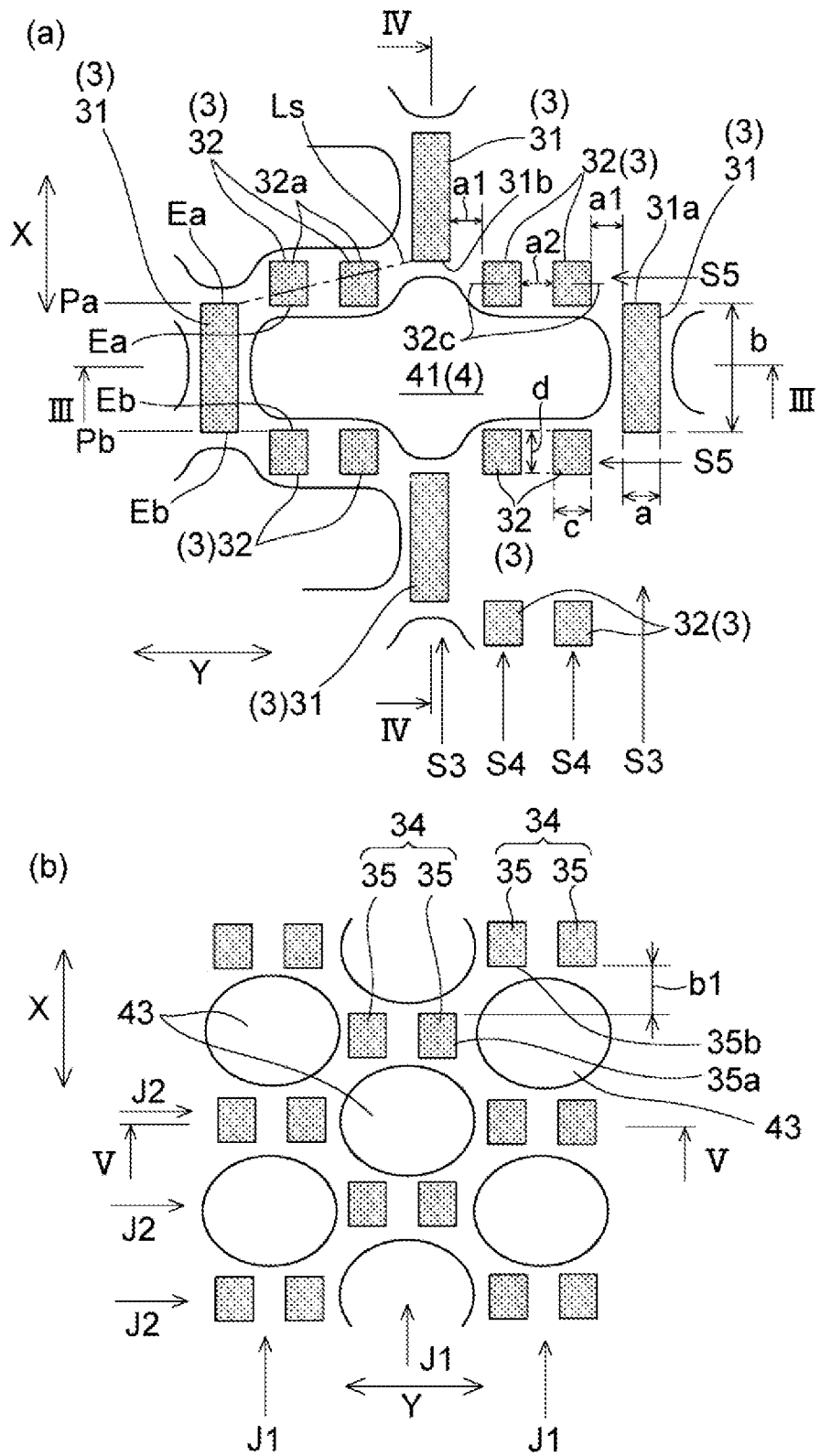

[Fig. 6]
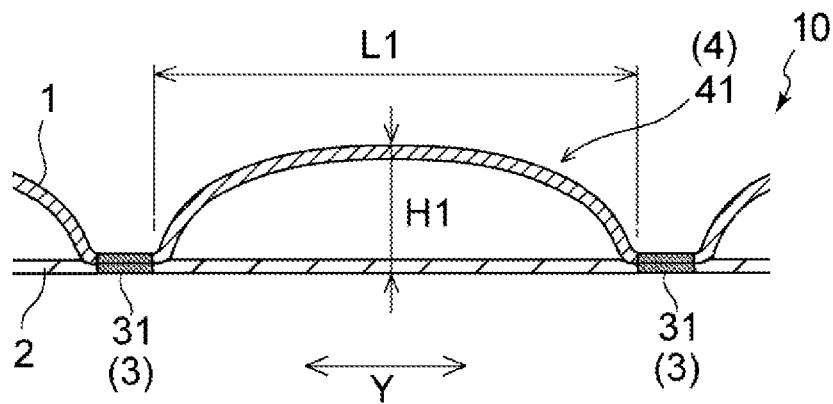
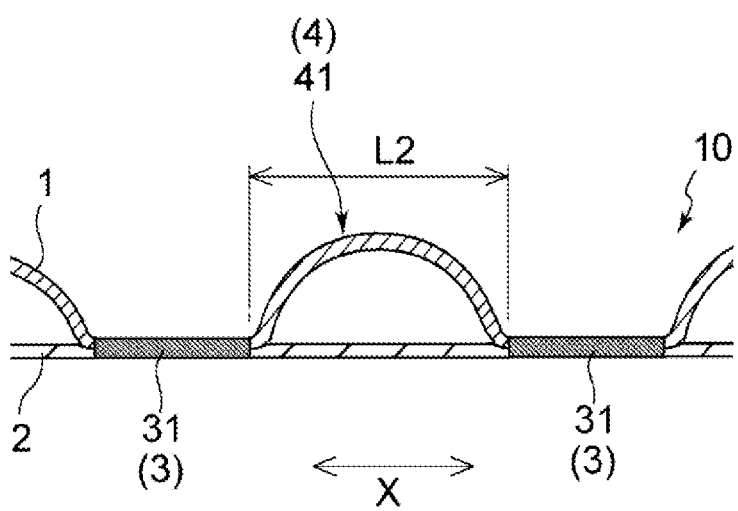
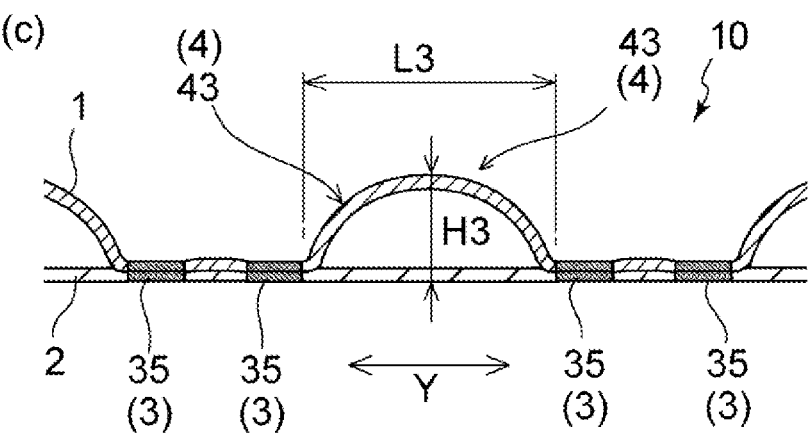

[Fig. 7]
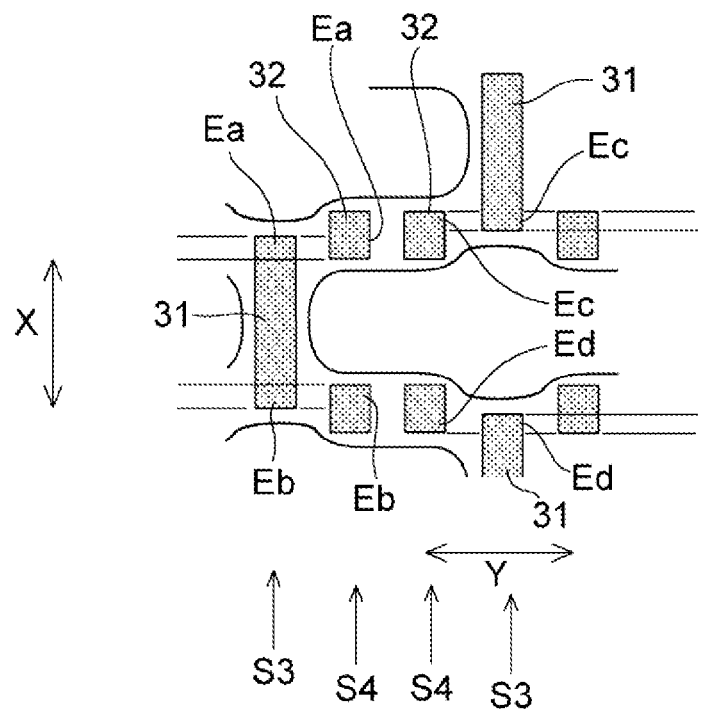
[Fig. 8]
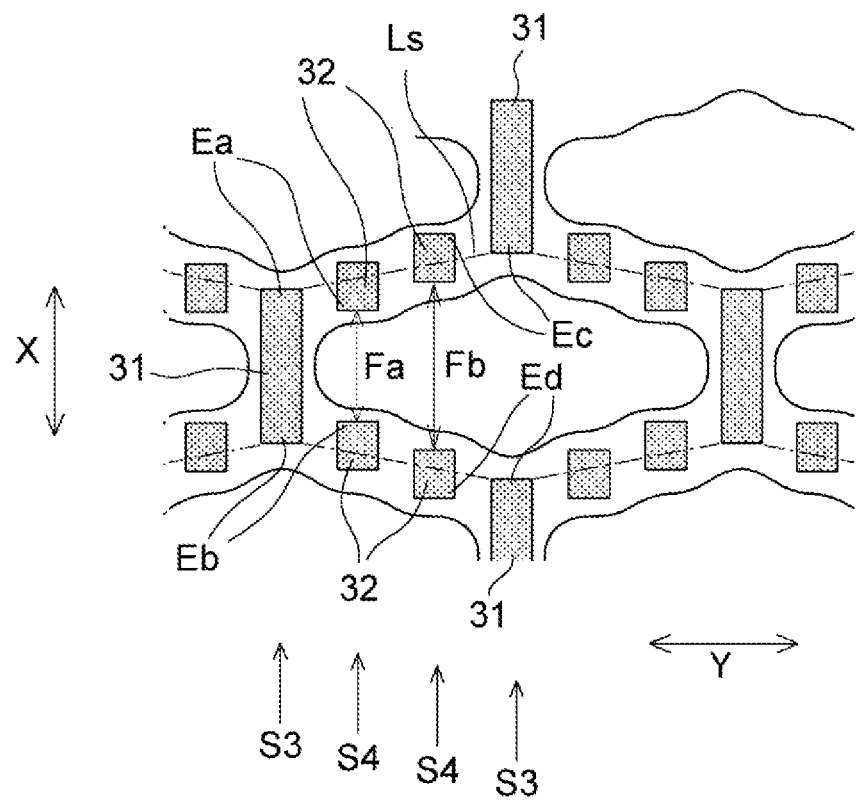

ABSORBENT ARTICLE

TECHNICAL FIELD

The present invention relates to an absorbent article such as a disposable diaper, a sanitary napkin, or an adult incontinence pad.

BACKGROUND ART

Conventionally, a technique for an absorbent article such as a disposable diaper is known in which the skin-facing surface side of the topsheet is formed to have a three-dimensional shape in regards to reducing the contact area and friction between the topsheet and the skin of the wearer and improving the texture and the air permeability.

The applicant of the present invention has already proposed the use of a composite sheet as the topsheet of an absorbent article, the composite sheet being a sheet in which a first sheet and a second sheet that are stacked are bonded to each other at a plurality of bonding portions, and a projection that protrudes toward the skin of the wearer are formed by the first sheet protruding in a direction away from the second sheet at a portion other than the bonding portions.

For example, the applicant of the present invention has proposed, in Patent Literature 1, an absorbent article that includes a topsheet that is made of a composite sheet, wherein projections are formed in a dispersed manner in the composite sheet, each projection of the composite sheet is composed of: a high projection that has a hollow portion on the back side and forms an apex of the projection; and four low projections that are formed around the high projection so as to lie over the high projection, and the projection is surrounded by a plurality of bonding portions. The applicant of the present invention has also proposed, in Patent Literature 2, an absorbent article that uses, as the topsheet, a composite sheet in which a plurality of central continuous projections that extend in a width direction of the absorbent article are aligned in a longitudinal direction of the absorbent article in a plurality of rows in a central region that is located at the center in the width direction of the absorbent article.

CITATION LIST

Patent Literature

Patent Literature 1: JP 2016-116584 A
Patent Literature 2: JP 2016-116582 A

SUMMARY OF INVENTION

The present invention relates to an absorbent article that includes: a topsheet that comprises a composite sheet; a backsheet; and an absorbent member that is provided between the topsheet and the backsheet, and has a longitudinal direction that corresponds to a front-back direction of a wearer, and a width direction that is perpendicular to the longitudinal direction. The composite sheet includes a first sheet and a second sheet that are stacked, the first sheet and the second sheet are bonded to each other at a plurality of bonding portions, and projections that protrude toward a skin of the wearer are formed by the first sheet protruding in a direction away from the second sheet at portions other than the bonding portions. In the composite sheet, a plurality of first oblique bonding portion rows in each of which the plurality of bonding portions are aligned in a first direction that is oblique to both the longitudinal direction and the width direction, and a plurality of second oblique bonding portion rows in each of which the plurality of bonding portions are aligned in a second direction that is oblique to both the longitudinal direction and the width direction and that intersects the first direction are formed. A long bonding portion that is elongated in the longitudinal direction is formed at each intersection of the first oblique bonding portion rows and the second oblique bonding portion rows. As the projections, laterally long projections that are elongated in the width direction are formed in a dispersed manner in the longitudinal direction and the width direction. Each of the laterally long projections is surrounded by two first oblique bonding portion rows and two second oblique bonding portion rows, and the long bonding portion is formed between the laterally long projections that are adjacent in the width direction.

BRIEF DESCRIPTION OF DRAWINGS

FIG. 1 is a plan view showing a basic configuration of a disposable diaper that is an absorbent article according to one embodiment of the present invention.

FIG. 2 is a cross sectional view taken along the line II-II shown in FIG. 1.

FIG. 3 is a plan view of a topsheet (composite sheet) of a disposable diaper according to a first embodiment.

FIG. 4 is an enlarged plan view showing a portion of the composite sheet used as the topsheet in the first embodiment.

FIG. 5(a) is a further enlarged plan view showing a portion of a central region M of the composite sheet shown in FIG. 4, and FIG. 5(b) is a further enlarged plan view showing a portion of a side region S of the composite sheet 10.

FIGS. 6(a) to 6(c) are enlarged cross sectional views showing cross sections taken along a thickness direction of the topsheet (composite sheet) shown in FIG. 3, with FIG. 6(a) being a cross sectional view taken along the line shown in FIG. 5(a), FIG. 6(b) being a cross sectional view taken along the line IV-IV shown in FIG. 5(a), and FIG. 6(c) being a cross sectional view taken along the line V-V shown in FIG. 5(b). FIGS. 6(a) to 6(b) may also be collectively referred to as FIG. 6.

FIG. 7 is an illustrative diagram of a relevant part of another embodiment of the present invention.

FIG. 8 is an illustrative diagram of a relevant part of still another embodiment of the present invention.

DESCRIPTION OF EMBODIMENTS

According to the absorbent article of Patent Literature 1, even if the composite sheet that constitutes the topsheet is bent while the absorbent article is worn, the low projections are flattened before the central high projection is flattened, and thus the central high projection is unlikely to be flattened. Accordingly, with the projections, good texture, back leakage prevention effect, and good air permeability are maintained.

The projections of the composite sheet used in Patent Literature 1 have excellent shape retention property. However, when a misalignment in a direction extending along the longitudinal direction of the diaper occurs between the topsheet and the skin of the wearer while the diaper is worn, a rub may occur between the projections and the skin. On the other hand, with the absorbent article of Patent Literature 2, when a misalignment in a direction extending along the longitudinal direction of the diaper occurs between the topsheet and the skin of the wearer, the central continuous projections are follow-up deformed so as to be flattened in the longitudinal direction along with a change in the relative position of the skin. Accordingly, it is possible to reduce the degree to which the skin is rubbed.

However, in the composite sheet used in the absorbent article of Patent Literature 2, the central continuous projections are preferably formed between embossed regions that extend in the width direction of the absorbent article, and thus liquid excrement is likely to spread along the embossed regions or the central continuous projections and in the width direction of the absorbent article. Accordingly, depending on the configuration of the side regions, it may give the user a sense of wetness around the legs. Also, it may make it difficult to further improve the leakage prevention performance.

The present invention relates to an absorbent article that can overcome the disadvantages of the conventional technology described above.

Hereinafter, the present invention will be described by way of a preferred embodiment with reference to the drawings.

FIGS. 1 and 2 show a basic structure of a disposable diaper 100 (hereinafter also referred to simply as "diaper 100") that is an absorbent article according to one embodiment of the present invention.

As shown in FIGS. 1 and 2, the diaper 100 includes a liquid-permeable topsheet 12, a liquid-impermeable backsheet 13, and an absorbent member 14 that is provided between the topsheet 12 and the backsheet 13. With respect to the backsheet 13, the term "liquid-impermeable" refers to the concept that also includes a backsheet 13 that is less liquid permeable, and encompasses a backsheet 13 that does not at all allow a liquid to pass therethrough, and a backsheet 13 that is made of a water-repellent sheet or the like.

The diaper 100 has a longitudinal direction X that corresponds to the front-back direction of the wearer, and a width direction Y that is perpendicular to the longitudinal direction X when the diaper 100 is flattened out as shown in FIG. 1. Also, the diaper 100 includes, in the longitudinal direction X, a front portion A that is to be placed on an abdominal side of the wearer when the diaper 100 is worn, a rear portion B that is to be placed on a dorsal side of the wearer when the diaper 100 is worn, and a crotch portion C that is provided between the front portion A and the rear portion B. The diaper 100 is an open-type disposable diaper. Fastening tapes 17 are provided at two side edge portions of the rear portion B, and a landing zone 18 where the fastening tapes 17 are fixed is provided on an outer surface of the front portion A.

The absorbent member 14 of the diaper 100 includes an absorbent core 14a and a core wrap sheet 14b that wraps the absorbent core 14a. The absorbent core 14a may be made of, for example, a laminated fiber body composed of liquid-absorbent fibers such as pulp fibers, or a mixed laminated fiber body composed of liquid-absorbent fibers and water-absorbent polymers. Examples of the liquid-absorbent fibers include pulp fibers, rayon fibers, cotton fibers, and cellulosic hydrophilic fibers such as cellulose acetate fibers. Other than the cellulosic hydrophilic fibers, it is also possible to use fibers obtained by hydrophilizing fibers made of synthetic resin such as polyolefin, polyester, or polyamide with a surfactant or the like. As the core wrap sheet 14b, for example, tissue paper or a water-permeable non-woven fabric is used. The core wrap sheet 14b may be a single sheet that wraps the entire absorbent core 14a, or may be a combination of two or more sheets that wrap the absorbent core 14a. As the backsheet 13, a liquid-impermeable or water-repellent resin film, a laminate sheet that is composed of a resin film and a non-woven fabric, or the like is used.

On each side of the diaper 100 in the longitudinal direction X, a three-dimensional gathers-forming sheet 15 that includes an elastic member 15a is provided. Upon contraction of the elastic member 15a, three-dimensional gathers that stand upright toward the skin of the wearer are formed in the crotch portion C when the diaper 100 is worn. Also, in a portion of the crotch portion C that is to be placed around a leg, a leg portion elastic member 16 is provided in a stretched state. Upon contraction of the leg portion elastic member 16, legs gathers that improve the fit to the leg of the wearer are formed in the crotch portion C when the diaper 100 is worn.

The topsheet 12 of the disposable diaper 100 according to the first embodiment is made of a composite sheet 10 shown in FIG. 3.

As shown in FIG. 3, the composite sheet 10 includes a central region M in which bonding portions 3 and the projections 4 are formed in mutually different patterns, and a pair of side regions S and S that are provided on two opposing sides of the central region M. The central region M is located at the center of the diaper 100 in the width direction Y, and the pair of side regions S and S are formed on two opposing outer sides in the width direction Y across the central region M. The pair of side regions S and S are formed along two side portions of the composite sheet 10 in the longitudinal direction X of the diaper 100.

FIG. 4 is an enlarged plan view showing a portion of the composite sheet 10. FIG. 5($a$) is a further enlarged plan view showing a portion of the central region M of the composite sheet 10, and FIG. 5($b$) is a further enlarged plan view showing a portion of the side region S of the composite sheet 10. FIG. 4 shows a portion of the composite sheet 10 that is to be disposed on the crotch portion C. The side regions S are formed at symmetric positions with respect to a longitudinal center line CL that extends in the longitudinal direction X of the diaper 100, and in each side region S, projections and recesses are formed in the same pattern.

As shown in FIGS. 5 and 6, in the composite sheet 10, in the central region M and each of the side regions S, a first sheet 1 and a second sheet 2 that are stacked are partially bonded by embossing processing, and thereby a plurality of bonding portions 3 are formed. The first sheet 1 and the second sheet 2 that are stacked are bonded to each other at the plurality of bonding portions 3. Also, in the central region M and each of the side regions S, projections 4 that protrude toward the skin of the wearer are each formed by the first sheet 1 protruding in a direction away from the second sheet 2 at a portion other than the bonding portions 3. The composite sheet 10 is configured such that, in the central region M and each of the side regions S, its surface that is on the second sheet 2 side is substantially flat, and large projections and recesses are formed on its surface that is on the first sheet 1 side.

The first sheet 1 and the second sheet 2 are made of sheet materials. As the sheet materials, it is possible to use, for example, fiber sheets such as non-woven fabrics, woven fabrics and knitted fabrics, films, and the like. From the viewpoint of texture and the like, it is preferable to use fiber sheets. In particular, it is preferable to use non-woven fabrics. The sheet materials that constitute the first sheet 1 and the second sheet 2 may be of the same type, or may be of different types.

In the case where a non-woven fabric is used as the sheet material for constituting each of the first sheet 1 and the second sheet 2, examples of the non-woven fabric include an air-through non-woven fabric, a spunbond non-woven fabric, a spunlace non-woven fabric, a melt-blown non-woven fabric, a resin bonded non-woven fabric, and a needle punched non-woven fabric. It is also possible to use a stack obtained by combining two or more of the non-woven fabrics listed above, or a stack obtained by combining a non-woven fabric as listed above with a film or the like. Among the non-woven fabrics listed above, it is preferable use an air-through non-woven fabric, or a spunbond non-woven fabric. The non-woven fabric that is used as the sheet material for constituting each of the first sheet 1 and the second sheet 2 has a basis weight of preferably 10 g/m² or more, more preferably 15 g/m² or more, and preferably 40 g/m² or less, more preferably 35 g/m² or less. The non-woven fabric has a basis weight of preferably 10 g/m² or more and 40 g/m² or less, and more preferably 15 g/m² or more and 35 g/m² or less.

As the fibers that constitute the non-woven fabric, fibers made of any type of thermoplastic resin can be used. Examples of thermoplastic resin include polyolefins such as polyethylene and polypropylene, polyesters such as polyethylene terephthalate, polyamides such as nylon 6 and nylon 66, poly(acrylic acid), polymethacrylic acid alkyl ester, poly(vinyl chloride), and polyvinylidene chloride. These resins may be used alone or as a blend containing a combination of two or more. Also, these resins may be used in the form of composite fibers such as core-in-sheath composite fibers or side-by-side composite fibers.

In the central region M of the composite sheet 10, as shown in FIG. 4, the bonding portions 3 that are formed by bonding the first sheet 1 and the second sheet 2 each form a plurality of rows: a first oblique bonding portion row S1 in which a plurality of the bonding portions 3 are aligned in a first direction D1 that is oblique to both the longitudinal direction X and the width direction Y; and a second oblique bonding portion row S2 in which a plurality of the bonding portions 3 that are aligned in a second direction D2 that is oblique to both the longitudinal direction X and the width direction Y and that intersects the first direction D1.

At the intersections of the first oblique bonding portion row S1 and the second oblique bonding portion row S2, long bonding portions 31 that are elongated in the longitudinal direction X are formed. The first oblique bonding portion row S1 and the second oblique bonding portion row S2 of the present embodiment have intersections that are spaced apart at a regular interval in the first direction D1 and the second direction D2, respectively, and one long bonding portion 31 is provided at each intersection. The first direction D1 has an inclination angle θ1 with respect to the longitudinal center line CL of preferably 45° or more and 80° or less, and more preferably 50° or more and 70° or less. The second direction D2 has an inclination angle θ2 with respect to the longitudinal center line CL of preferably 45° or more and 80° or less, and more preferably 50° or more and 70° or less. The first direction D1 and the second direction D2 are preferably line-symmetric with respect to a symmetry line that is a straight line parallel to the longitudinal center line CL.

Also, in the composite sheet 10, as the projections 4, laterally long projections 41 that are elongated in the width direction Y are formed in a dispersed manner in the longitudinal direction X and the width direction Y.

The laterally long projections 41 are disposed in a staggered manner. To be more specific, as shown in FIG. 4, the laterally long projections 41 are disposed so as to form: a longitudinal direction projection row R3 in which a plurality of the laterally long projections 41 are aligned at a regular interval in the longitudinal direction X; a width direction projection row R4 in which a plurality of the laterally long projections 41 are aligned at a regular interval in the width direction Y; a first direction projection row R5 in which a plurality of the laterally long projections 41 are aligned at a regular interval in the first direction D1: and a second direction projection row R6 in which a plurality of the laterally long projections 41 are aligned at a regular interval in the second direction D2.

Between adjacent longitudinal direction projection rows R3 in the width direction Y, the placement positions of the laterally long projections 41 are displaced by a half-pitch in the longitudinal direction X. Also, between adjacent width direction projection rows R4 in the longitudinal direction X, the placement positions of the laterally long projections 41 are displaced by a half-pitch in the width direction Y.

Also, short bonding portions 32 that each have a length in the longitudinal direction X that is shorter than the length in the longitudinal direction of the long bonding portions 31 are provided between adjacent long bonding portions 31 in each of the first oblique bonding portion row S1 and the second oblique bonding portion row S2. As shown in FIG. 5(a), the short bonding portions 32 provided between adjacent long bonding portions 31 preferably have an overlapping portion that overlaps a straight line Ls that is the shortest line connecting two long bonding portions 31 in adjacent longitudinal direction long bonding portion rows S3 that are adjacent in the width direction Y.

As shown in FIG. 5(a), the short bonding portions 32 according to the present embodiment are formed in a plurality of rows: a longitudinal direction short bonding portion row S4 in which a plurality of the short bonding portions 32 are spaced apart at regular intervals and aligned in the longitudinal direction X; and a width direction short bonding portion row S5 in which a plurality of the short bonding portions 32 are spaced apart at regular intervals and aligned in the width direction Y.

Also, the longitudinal direction short bonding portion rows S4 that are adjacent in the width direction Y are provided between the longitudinal direction long bonding portion rows S3 that are adjacent in the width direction Y.

It is preferable that a spacing a1 between the longitudinal direction short bonding portion row S4 and the longitudinal direction long bonding portion row S3 that are adjacent in the width direction Y and a spacing a2 between the longitudinal direction short bonding portion rows S4 in the case where two or more longitudinal direction short bonding portion rows S4 are provided between adjacent longitudinal direction long bonding portion rows S3 are equal.

Also, in each longitudinal direction short bonding portion row S4 that is provided between adjacent longitudinal direction long bonding portion rows S3, a center position 32c of each short bonding portion 32 in the longitudinal direction X is located between an end 31a of one long bonding portion 31 of one of the longitudinal direction long bonding portion rows S3 and an end 31b of one long bonding portion 31 of the other longitudinal direction long bonding portion row S3.

As shown in FIG. 4, each individual laterally long projection 41 of the present embodiment is formed so that it is surrounded by two first oblique bonding portion rows S1 and S1 and two second oblique bonding portion rows S2 and S2. More specifically, each individual laterally long projection 41 is formed within a region surrounded by four long bonding portions 31 at the intersections of the first oblique bonding portion row S1 and the second oblique bonding portion row S2 and four or more short bonding portions 32 provided between the four long bonding portions 31, more specifically, eight short bonding portions 32.

Also, as shown in FIG. 5(a), each individual laterally long projection 41 of the present embodiment is configured such that a long bonding portion 31 that is elongated in the longitudinal direction X is formed between adjacent laterally long projections 41 and 41 in the width direction Y.

To be more specific, in the composite sheet 10, as shown in FIG. 4, a plurality of width direction composite rows R9 in each of which laterally long projections 41 and long bonding portions 31 are alternately disposed in the width direction Y are formed in the longitudinal direction X. Between adjacent width direction composite rows R9 in the longitudinal direction X, the position of each laterally long projection 41 and the position of each long bonding portion 31 are displaced by a half-pitch in the width direction Y.

In the pair of side regions S and S of the composite sheet 10, projections 4 are formed in a different pattern from the pattern of the projections 4 formed in the central region M. As used herein, the expression "projections are formed in a different pattern" encompasses the case where only the arrangement of the projections is different, the case where the form of the projections is different, and the case where both the arrangement and the form of the projections are different. The case where the arrangement of the projections is different also encompasses the case where the distance between projections is different. Likewise, the case where the form of the projections is different also encompasses the case where the projections have a different shape when viewed in a plan view. In the composite sheet 10 according to the present embodiment, the arrangement and the form of the projections are different between the central region M and the pair of side regions S and S.

Also, in each of the bonding portions 3 in the central region M and the side regions S, the constituent resin of the constituent fibers of either one or both of the first sheet 1 and the second sheet 2 is melt-solidified. Also, in each bonding portion 3, the first sheet 1 and the second sheet 2 are highly densified as compared with other portions (portions other than the bonding portion). That is, each bonding portion 3 of the composite sheet 10 is preferably a thermally fused portion that is formed by integrally heating and pressurizing the first sheet 1 and the second sheet 2, and in which the two sheets are bonded to each other through melting and subsequent solidification of the constituent resin of the constituent fibers of either one or both of the first sheet 1 and the second sheet 2. In each bonding portion 3, the first sheet 1 and the second sheet 2 are preferably both melt-solidified. Also, in the central region M and each of the side regions S, each bonding portion 3 may be formed by bonding the first sheet 1 and the second sheet 2 with a bonding means, other than thermal fusing, such as a hot melt adhesive or any other adhesive.

In the diaper 100 according to the first embodiment, as the topsheet 12, a composite sheet 10 is used in which the first sheet 1 protrudes in a direction away from the second sheet 2 at portions other than bonding portions 3 so as to form projections 4 that protrude toward the skin of the wearer. Accordingly, good shape retention property of the projections 4 can be obtained due to the presence of the second sheet 2 while achieving a soft skin-facing surface, and it is also possible to obtain back leakage prevention effect of preventing a liquid that has been absorbed by the absorbent member 14 from leaking back to the skin of the wearer, and excellent air permeability.

Similar to ordinary diapers, in the diaper 100 according to the first embodiment, a misalignment in a direction extending along the longitudinal direction X is likely to occur between the topsheet 12 at the center in the width direction of the diaper and the skin of the wearer by movement of the legs or the like while the diaper is worn. However, in the diaper 100 according to the first embodiment, the central region M of the composite sheet 10 is provided at the center in the width direction of the diaper, and the laterally long projections 41 are flattened in the longitudinal direction X along with a change in the relative position of the skin, and deform and conform to the change. Accordingly, it is possible to reduce the degree to which the skin is rubbed by the laterally long projections 41.

In addition thereto, a long bonding portion 31 that is elongated in the longitudinal direction X is formed between adjacent laterally long projections 41 in the width direction Y. Therefore, it is possible to reduce the occurrence of a problem caused by liquid excrement such as urine excessively spreading in the width direction Y, which is likely to occur when the amount of liquid excrement is large, as compared with a configuration in which continuous projections that continuously extend in the width direction Y are formed, or embossed regions that extend in the width direction Y are formed in order to form the continuous projections. It is possible to effectively prevent, for example, the occurrence of side leakage, and the wearer from feeling a sense of wetness around the legs that are likely to occur as a result of liquid excrement excessively spreading in the width direction.

Also, the disposable diaper 100 according to the present embodiment includes short bonding portions 32 in addition to the long bonding portions 31, and also includes a plurality of types of bonding portions 3 that have different lengths in the longitudinal direction X as the bonding portions 3 that bond the first sheet 1 and the second sheet 2. With this configuration, the area ratio of the projections 4 per unit area of the topsheet 12 is increased, and thus the texture is improved.

From the viewpoint of more reliably achieving one or more advantageous effects described above, the projections of the composite sheet 10 preferably have the following configuration.

With respect to the laterally long projection 41, the ratio (L1/L2) of the length L1 in the width direction Y (see FIG. 6(a)) to the length L2 in the longitudinal direction X (see FIG. 6(b)) is preferably 1.1 or more, more preferably 1.5 or more, and preferably 6.0 or less, more preferably 4.0 or less, and preferably 1.1 or more and 6.0 or less, more preferably 1.5 or more and 4.0 or less. The laterally long projection 41 has a length L1 in the width direction Y of preferably 3 mm or more, more preferably 5 mm or more, and preferably 30 mm or less, more preferably 15 mm or less, and preferably 3 mm or more and 30 mm or less, more preferably 5 mm or more and 15 mm or less.

The length L1 in the width direction Y of the laterally long projection 41 is the distance between long bonding portions 31 in the width direction composite row R9, and the length L2 in the longitudinal direction X of the laterally long projection 41 has the same distance as the distance between long bonding portions 31 in the longitudinal direction long bonding portion row S3.

The laterally long projection 41 has a H1 (see FIG. 6(a)) of preferably 0.5 mm or more, more preferably 1.0 mm or more, and preferably 5.0 mm or less, more preferably 4.0 mm or less, and preferably 0.5 mm or more and 5.0 mm or less, more preferably 1.0 mm or more and 4.0 mm or less.

Also, each projection 43 formed in the side region S (see FIG. 6(c)) has a height H3 of preferably 0.3 mm or more, more preferably 0.6 mm or more, and preferably 4.0 mm or less, more preferably 3.0 mm or less, and preferably 0.3 mm or more and 4.0 mm or less, more preferably 0.6 mm or more and 3.0 mm or less.

As used herein, the height of the projection 4 of the composite sheet refers to, as shown in FIGS. 6(a) and 6(c), the distance from the lower surface of the second sheet 2 to the upper surface of the first sheet 1. Also, the height is a value obtained by observing a cross section of each projection with a digital microscope (available from Keyence Corporation), and measuring the shortest distance between the lower surface of the second sheet 2 and the apex of the projection.

Also, the long bonding portion 31 has a length b in the longitudinal direction X that is preferably 40% or more, more preferably 50% or more, and preferably 100% or less, more preferably 80% or less, and preferably 40% or more and 100% or less, more preferably 50% or more and 80% or less of the length L2 in the longitudinal direction X of the laterally long projection 41.

Also, in the long bonding portion 31, the ratio (b/a) of the length b in the longitudinal direction X to the length a in the width direction Y is preferably 1.2 or more, more preferably 1.5 or more, and preferably 5.0 or less, more preferably 3.0 or less, and preferably 1.2 or more and 5.0 or less, more preferably 1.5 or more and 3.0 or less.

Also, the long bonding portion 31 has a length b in the longitudinal direction X of preferably 0.5 mm or more, more preferably 1.0 mm or more, and preferably 6.0 mm or less, more preferably 4.0 mm or less, and preferably 0.5 mm or more and 6.0 mm or less, more preferably 1.0 mm or more and 4.0 mm or less.

Also, with respect to each short bonding portion 32 provided between adjacent long bonding portions 31 in each of the first oblique bonding portion row S1 and the second oblique bonding portion row S2, the ratio (c/d) of the length c in the width direction Y to the length d in the longitudinal direction X is preferably 0.8 or more, more preferably 0.9 or more, and preferably 1.2 or less, more preferably 1.1 or less, and preferably 0.8 or more and 1.2 or less, more preferably 0.9 or more and 1.1 or less.

The short bonding portion 32 preferably has a length in the longitudinal direction X and a length in the width direction Y that are substantially the same. As used herein, the expression "a length in the longitudinal direction X and a length in the width direction Y that are substantially the same" means that the ratio (c/d) described above is 0.8 or more and 1.2 or less.

Also, the distance between short bonding portions 32 provided on two opposing sides of one laterally long projection 41 in the longitudinal direction X across the laterally long projections 41 (the distance in the up down direction in FIG. 5) is preferably 30% or more, more preferably 40% or more, and preferably 100% or less, more preferably 70% or less, and preferably 30% or more and 100% or less, more preferably 40% or more and 70% or less of the distance L2 between long bonding portions 31 in the longitudinal direction long bonding portion row S3 (see FIG. 6(b)).

Also, in the present embodiment, as shown in FIG. 5(a), one individual laterally long projection 41 is provided between a total of ten bonding portions 3 (five on each side) in the longitudinal direction X, and the laterally long projection 41 is surrounded by a total of twelve bonding portions 3 including two long bonding portions 31 that are provided on two opposing sides in the width direction Y. The number of bonding portions 3 that surround the laterally long projection 41 is preferably four or more, more preferably eight or more, and preferably twenty or less, more preferably sixteen or less. Such a plurality of bonding portions 3 are preferably provided in a pair between which a laterally long projection 41 is provided in the longitudinal direction X.

Also, in the composite sheet 10 according to the present embodiment, as shown in FIG. 5(a), longitudinal direction bonding portion rows S3 and S4 in each of which bonding portions 3 are spaced apart and aligned in the longitudinal direction X are formed in a plurality of rows in the width direction Y. The bonding portions 3 in adjacent longitudinal direction bonding portion rows in the width direction Y partially or entirely overlap in the longitudinal direction X, or the positions of the end portions of the bonding portions 3 match in the longitudinal direction X.

Specifically, as shown in FIG. 5(a), end portions Ea and Eb in the longitudinal direction X of a long bonding portion 31 in a longitudinal direction long bonding portion row S3 match the end portions of short bonding portions 32 in a longitudinal direction short bonding portion row S4 that is adjacent to the longitudinal direction long bonding portion row S3 in the width direction Y at positions Pa and Pb. Also, the short bonding portions 32 in adjacent longitudinal direction short bonding portion rows S4 in the width direction Y all overlap with each other in the longitudinal direction X.

Also, in an embodiment shown in FIG. 7, a long bonding portion 31 in a longitudinal direction long bonding portion row S3 and short bonding portions 32 in a longitudinal direction short bonding portion row S4 that is adjacent to the longitudinal direction long bonding portion row S3 in the width direction Y overlap at Ea and Eb that are portions near the end portions in the longitudinal direction X. Also, the short bonding portions 32 in adjacent longitudinal direction short bonding portion rows S4 in the width direction Y all overlap with each other in the longitudinal direction X.

As described above, when the bonding portions in adjacent longitudinal direction bonding portion rows in the width direction Y partially or entirely overlap in the longitudinal direction X, or the positions of the end portions of the bonding portions match in the longitudinal direction X, projections and recesses are easily formed in the longitudinal direction X between the longitudinal direction long bonding portion row S3 and the longitudinal direction short bonding portion row S4, and between longitudinal direction short bonding portion rows S4, and thus the movement of the laterally long projections 41 in the longitudinal direction X is improved, and it is possible to further reduce the friction on the skin due to the laterally long projections 41 when a misalignment in a direction extending along the longitudinal direction X has occurred between the topsheet 12 and the skin of the wearer while the diaper 1 is worn.

In the example shown in FIG. 7, longitudinal direction short bonding portion rows S4 are formed between the longitudinal direction long bonding portion rows S3 that are adjacent in the width direction Y, and end portions Ea and Eb of a long bonding portions 31 of one of the longitudinal direction long bonding portion rows S3 respectively overlap near end portions Ea and Eb that are portions in the longitudinal direction of short bonding portions 32 in the longitudinal direction short bonding portion row S4 that is adjacent to the longitudinal direction long bonding portion row S3. Also, end portions Ec and Ed of a long bonding portions 31 of the other longitudinal direction long bonding portion row S3 respectively overlap near end portions Ec and Ed that are portions in the longitudinal direction of short bonding portions 32 in the longitudinal direction short bonding portion row S4 that is adjacent to the longitudinal direction long bonding portion row S3.

Also, in the case where a plurality of longitudinal direction short bonding portion rows S4 are present between adjacent longitudinal direction long bonding portion rows S3 in the width direction Y as in the composite sheet 10 according to the present embodiment, in the plurality of longitudinal direction short bonding portion rows S4, as shown in FIG. 8, a distance Fa between short bonding portions 32 between which a laterally long projection 41 is interposed in one of the plurality of longitudinal direction short bonding portion rows S4 and a distance Fb between short bonding portions 32 between which the laterally long projection 41 is interposed in the other longitudinal direction short bonding portion row S4 may be mutually different. With this pattern, the recess portions along the first oblique bonding portion row S1 and the second oblique bonding portion row S2 are more easily formed, the movement of the laterally long projections 41 in the longitudinal direction X is further improved, and the friction on the skin while the diaper 1 is worn can be further reduced.

In the embodiment shown in FIG. 8 as well, longitudinal direction bonding portion rows S3 and S4 in each of which bonding portions 3 are spaced apart and aligned in the longitudinal direction X are formed in a plurality of rows in the width direction Y, and a long bonding portion 31 in a longitudinal direction long bonding portion row S3 and short bonding portions 32 in a longitudinal direction short bonding portion row S4 that is adjacent to the longitudinal direction long bonding portion row S3 in the width direction Y overlap at Ea and Eb that are portions of the long bonding portion 31 and the short bonding portions 32 in the longitudinal direction X. Also, the short bonding portions 32 in adjacent longitudinal direction short bonding portion rows S4 in the width direction Y also partially overlap with each other in the longitudinal direction X.

As in the embodiments shown in FIGS. 5(a) and 8, the short bonding portions 32 in the longitudinal direction short bonding portion rows S4 disposed between two long bonding portions 31 in adjacent longitudinal direction long bonding portion rows S3 in the width direction Y preferably have an overlapping portion that overlaps a straight line Ls that is the shortest line connecting the two long bonding portions 31 in adjacent longitudinal direction long bonding portion rows S3 that are adjacent in the width direction Y.

As shown in FIG. 4, laterally long projections 41 that are formed in a dispersed manner in the longitudinal direction X and the width direction Y are configured such that adjacent laterally long projections in the plane direction share one or more of the bonding portions 31 and 32 that surround the adjacent laterally long projections. More specifically, adjacent laterally long projections 41 in the width direction Y share a long bonding portion 31 that is provided therebetween, and adjacent laterally long projections 41 in the first direction D1 or the second direction D2 share four bonding portions out of twelve bonding portions that surround the adjacent laterally long projections 41. Adjacent laterally long projections 41 in a longitudinal direction projection row R3 share one long bonding portion 31.

As described above, when laterally long projections 41 and bonding portions 31 and 32 that surround the laterally long projections 41 are formed such that adjacent laterally long projections in the plane direction share one or more of the bonding portions 31 and 32 that surround the adjacent laterally long projections, the ratio of the area of the projections 4 per unit area of the topsheet 12 is increased, and thus the texture is improved. Also, as a result of the laterally long projections 41 and the long bonding portions 31 being repeated in similar patterns, uniform spreadability of liquid is further improved. As used herein, the term "uniform spreadability of liquid" means that the property of a liquid uniformly spreading in all directions with respect to a discharge point without spreading concentratedly in a specific direction on the topsheet.

In the pair of side regions S and S of the composite sheet 10 according to the present embodiment, as shown in FIGS. 4, 5(b), and 6(c), as the projections 4 formed by the first sheet 1 protruding in a direction away from the second sheet 2 at portions other than the bonding portions 3, projections 43 that have a length in the width direction Y that is shorter than the length in the width direction Y of the laterally long projections 41 of the central region M are formed in a staggered arrangement. In each side region S of the composite sheet 10, bonding portion pairs 34, each including a pair of bonding portions 35 and 35 that are closely disposed at the same spacing as the spacing a2 between longitudinal direction short bonding portion rows S4 of the central region M described above, are formed such that a plurality of width direction composite rows J2 in each of which projections 43 and bonding portion pairs 34 are alternately disposed in the width direction Y at a regular interval, and a plurality of longitudinal direction composite rows J1 in each of which projections 43 and bonding portion pairs 34 are alternately disposed in the longitudinal direction X at a regular interval are formed.

At the center in the width direction, a central region M in which the bonding portions and the laterally long projections are formed in the above-described manner is formed, and in each of a pair of side regions S and S provided on two opposing sides of the central region M, projections 43 that have a length L3 in the width direction Y that is shorter than the length in the width direction Y of the laterally long projections 41 of the central region M are formed in a staggered arrangement. With this configuration, it is possible to more reliably prevent a liquid from excessively spreading in the width direction Y.

A composite sheet 10 that has the above-described configuration may be manufactured in the same manner as that disclosed in JP 2015-112343A or Patent Literature 1. Specifically, a strip-shaped first sheet 1 is fed between a first roll and a second roll whose circumferential surfaces are shaped to be engageable with each other, the first sheet 1 is deformed to have projections and recesses, then, the first sheet 1 is moved along the circumferential surface portion of the first roll from the engaging portion, and thereafter a second sheet 2 is fed such that the second sheet is placed on the first sheet 1. The two sheets 1 and 2 are compressed under heat between the projections on the first roll and a heat roll so as to partially bond the sheets. At this time, the shape of the projections and recesses of the first roll and the second roll, and the pattern of bonding portions formed by the first roll and the heat roll are changed between the central portion and the side portions of the first sheet. At the time when the first sheet 1 is deformed to have projections and recesses by feeding the first sheet into the engaging portion between the first roll and the second roll, it is preferable that the first sheet is pulled in a direction toward the inside of the rolls so as to facilitate the deformation of the first sheet 1 to have projections and recesses.

Up to here, the present invention has been described by way of a preferred embodiment thereof, but the present invention is not limited to the embodiment given above and can be modified as appropriate.

For example, the composite sheet 10 may not include the side regions S and S in which projections are formed in a pattern different from that used in the central region M. A composite sheet 10 that throughout has the same configuration as that of the central region M may be used as the topsheet 12.

Also, in the embodiment described above, as shown in FIG. 3, the central region M and the side regions S and S that are provided on two opposing sides of the central region M in which projections are formed in mutually different patterns are formed so as to extend over the entire length in the longitudinal direction of the diaper 100. However, in the absorbent article according to the present invention, the central region M including laterally long projections 41 and long bonding portions 31 that surround the laterally long projections 41 may be formed only in a portion in the longitudinal direction of the absorbent article. For example, the central region M may be formed only in the crotch portion C, only in the front portion A, or only in the rear portion B. Alternatively, the central region M may be formed only in the crotch portion C and the front portion A, or only in the crotch portion C and the rear portion B.

The shape and arrangement of the bonding portions 31 and 32 that surround the laterally long projections 41 and other bonding portions can be determined as appropriate. Each individual bonding portion may have, other than a rectangular shape or a square shape as shown in FIG. 3, any shape such as a circular, elliptic, oval, triangular, tetragonal, pentagonal, hexagonal, star, heart, or triangular shape.

Also, the absorbent article according to the present invention may be, instead of an open-type disposable diaper, a pant-type (pull-on type) disposable diaper. Alternatively the absorbent article according to the present invention may be a pant-type sanitary napkin or an ordinary non-pant-type sanitary napkin, or may be an adult incontinence pad, a panty liner, or the like.

With respect to the embodiment described above, the present invention further discloses the following absorbent articles.

<1>

An absorbent article including:

a topsheet that comprises a composite sheet;

a backsheet; and an absorbent member that is provided between the topsheet and the backsheet, the absorbent article having a longitudinal direction that corresponds to a front-back direction of a wearer, and a width direction that is perpendicular to the longitudinal direction, wherein the composite sheet includes a first sheet and a second sheet that are stacked, the first sheet and the second sheet are bonded to each other at a plurality of bonding portions, and projections that protrude toward a skin of the wearer are formed by the first sheet protruding in a direction away from the second sheet at portions other than the bonding portions, a plurality of first oblique bonding portion rows in each of which the plurality of bonding portions are aligned in a first direction that is oblique to both the longitudinal direction and the width direction, and a plurality of second oblique bonding portion rows in each of which the plurality of bonding portions are aligned in a second direction that is oblique to both the longitudinal direction and the width direction and that intersects the first direction are formed, a long bonding portion that is elongated in the longitudinal direction is formed at each intersection of the first oblique bonding portion rows and the second oblique bonding portion rows, as the projections, laterally long projections that are elongated in the width direction are formed in a dispersed manner in the longitudinal direction and the width direction, and each of the laterally long projections is surrounded by two first oblique bonding portion rows and two second oblique bonding portion rows, and the long bonding portion is formed between the laterally long projections that are adjacent in the width direction.

<2>

The absorbent article as set forth in clause <1>, wherein a plurality of types of bonding portions that have different lengths in the longitudinal direction are included as the bonding portions.

<3>

The absorbent article as set forth in clause <1> or <2>, wherein the first oblique bonding portion row and the second oblique bonding portion row include, between the intersections, a short bonding portion that has a length in the longitudinal direction that is shorter than a length in the longitudinal direction of the long bonding portion.

<4>

The absorbent article as set forth in any one of clauses <1> to <3>, wherein a plurality of longitudinal direction bonding portion rows in each of which the bonding portions are spaced apart and aligned in the longitudinal direction are formed in the width direction, and the bonding portions in the longitudinal direction bonding portion rows that are adjacent in the width direction partially or entirely overlap in the longitudinal direction, or positions of end portions of the bonding portions match in the longitudinal direction.

<5>

The absorbent article as set forth in any one of clauses <1> to <4>, wherein a plurality of width direction composite rows in each of which the laterally long projections and the long bonding portions are disposed alternately in the width direction are formed in the longitudinal direction, and positions of the long bonding portions in the width direction composite rows that are adjacent in the longitudinal direction are displaced by a half-pitch in the width direction.

<6>

The absorbent article as set forth in any one of clauses <1> to <5>, wherein the composite sheet is configured such that the laterally long projections that are adjacent in a plane direction share one or more of the bonding portions that surround each of the laterally long projections.

<7>

The absorbent article as set forth in any one of clauses <1> to <6>, wherein the first oblique bonding portion row S1 and the second oblique bonding portion row S2 have intersections at a regular interval in each of the first direction D1 and the second direction D2, and the long bonding portions 31 are disposed at the intersections.

<8>

The absorbent article as set forth in any one of clauses <1> to <7>, wherein the first direction D1 has an inclination angle θ1 with respect to a longitudinal center line CL of preferably 45° or more and 80° or less, and more preferably 50° or more and 70° or less.

<9>

The absorbent article as set forth in any one of clauses <1> to <8>, wherein the second direction D2 has an inclination angle θ2 with respect to a longitudinal center line CL of preferably 45° or more and 80° or less, and more preferably 50° or more and 70° or less.

<10>

The absorbent article as set forth in any one of clauses <1> to <9>, wherein the first direction D1 and the second direction D2 are line-symmetric with respect to a symmetry line that is a straight line parallel to a longitudinal center line CL.

<11>

The absorbent article as set forth in any one of clauses <1> to <10>, wherein the laterally long projections 41 are disposed so as to form: a longitudinal direction projection row R3 in which a plurality of the laterally long projections 41 are aligned at a regular interval in the longitudinal direction X: a width direction projection row R4 in which a plurality of the laterally long projections 41 are aligned at a regular interval in the width direction Y; a first direction projection row R5 in which a plurality of the laterally long projections 41 are aligned at a regular interval in the first direction D1; and a second direction projection row R6 in which a plurality of the laterally long projections 41 are aligned at a regular interval in the second direction D2.

<12>

The absorbent article as set forth in any one of clauses <1> to <11>, wherein placement positions of the laterally long projections 41 are displaced by a half-pitch in the longitudinal direction X between the longitudinal direction projection rows R3 that are adjacent in the width direction Y, and placement positions of the laterally long projections 41 are displaced by a half-pitch in the width direction Y between the width direction projection rows that are adjacent in the longitudinal direction X.

<13>

The absorbent article as set forth in any one of clauses <1> to <12>, wherein when two or more of the longitudinal direction short bonding portion rows S4 are provided between the longitudinal direction long bonding portion rows S3, a spacing a1 between the longitudinal direction short bonding portion row S4 and the longitudinal direction long bonding portion row S3 that are adjacent in the width direction Y is equal to a spacing a2 between the longitudinal direction short bonding portion rows S4.

<14>

The absorbent article as set forth in any one of clauses <1> to <13>, wherein in the longitudinal direction short bonding portion row S4 provided between the longitudinal direction long bonding portion rows S3, a center position 32c of the short bonding portion 32 in the longitudinal direction X is located between a first end 31a of the long bonding portion 31 of one of the longitudinal direction long bonding portion rows S3 and a second end 31b of the long bonding portion 31 of the other longitudinal direction long bonding portion row S3.

<15>

The absorbent article as set forth in any one of clauses <1> to <14>, wherein each of the laterally long projections 41 is formed within a region surrounded by four long bonding portions 31 that are provided at the intersections of the first oblique bonding portion row S1 and the second oblique bonding portion row S2 and four or more, more specifically eight short bonding portions 32 that are provided between the four long bonding portions 31.

<16>

The absorbent article as set forth in any one of clauses <1> to <15>, wherein each of the laterally long projections 41 is configured such that the long bonding portion 31 that is elongated in the longitudinal direction X is formed between the laterally long projections 41 and 41 that are adjacent in the width direction Y.

<17>

The absorbent article as set forth in any one of clauses <1> to <16>, wherein the laterally long projections 41 have a ratio (L1/L2), which is a ratio of a length L1 in the width direction Y to a length L2 in the longitudinal direction X, of preferably 1.1 or more, more preferably 1.5 or more, and preferably 6.0 or less, more preferably 4.0 or less.

<18>

The absorbent article as set forth in any one of clauses <1> to <17>, wherein the laterally long projections 41 have a length L1 in the width direction Y of preferably 3 mm or more, more preferably 5 mm or more, and preferably 30 mm or less, more preferably 15 mm or less.

<19>

The absorbent article as set forth in any one of clauses <1> to <18>, wherein a length L1 in the width direction Y of the laterally long projections 41 is a distance between the long bonding portions 31 in the width direction composite row R9, and the length L2 in the longitudinal direction X of the laterally long projections 41 is the same as a distance between the long bonding portions 31 in the longitudinal direction long bonding portion row S3.

<20>

The absorbent article as set forth in any one of clauses <1> to <19>, wherein the laterally long projections 41 have a height H1 of preferably 0.5 mm or more, more preferably 1.0 mm or more, and preferably 5.0 mm or less, more preferably 4.0 mm or less.

<21>

The absorbent article as set forth in any one of clauses <1> to <20>, wherein the long bonding portions 31 have a length b in the longitudinal direction X that is preferably 40% or more, more preferably 50% or more, and preferably 100% or less, more preferably 80% or less of the length L2 in the longitudinal direction X of the laterally long projections 41.

<22>

The absorbent article as set forth in any one of clauses <1> to <21>, wherein the long bonding portions 31 have a ratio (b/a), which is a ratio of a length b in the longitudinal direction X to a length a in the width direction Y, of preferably 1.2 or more, more preferably 1.5 or more, and preferably 5.0 or less, more preferably 3.0 or less.

<23>

The absorbent article as set forth in any one of clauses <1> to <22>, wherein the long bonding portions 31 have a length b in the longitudinal direction X of preferably 0.5 mm or more, more preferably 1.0 mm or more, and preferably 6.0 mm or less, more preferably 4.0 mm or less.

<24>
The absorbent article as set forth in any one of clauses <1> to <23>,
wherein the short bonding portions 32 provided between the long bonding portions 31 in each of the first oblique bonding portion row S1 and the second oblique bonding portion row S2 have a ratio (c/d), which is a ratio of a length c in the width direction Y to a length d in the longitudinal direction X, of preferably 0.8 or more, more preferably 0.9, and preferably 1.2 or less, more preferably 1.1 or less.
<25>
The absorbent article as set forth in any one of clauses <1> to <24>,
wherein the short bonding portions 32 have a length in the longitudinal direction X and a length in the width direction Y that are substantially the same.
<26>
The absorbent article as set forth in any one of clauses <1> to <25>,
wherein a distance between the short bonding portions 32 provided on two opposing sides in the longitudinal direction X of the laterally long projection 41 across the laterally long projection 41 is 30% or more, more preferably 40% or more, and preferably 100% or less, more preferably 70% or less of a distance L2 between the long bonding portions 31 in the longitudinal direction long bonding portion row S3.
<27>
The absorbent article as set forth in any one of clauses <1> to <26>,
wherein the number of the bonding portions 3 that surround each of the laterally long projections 41 is preferably 4 or more, more preferably 8 or more, and preferably 20 or less, more preferably 16 or less.
<28>
The absorbent article as set forth in any one of clauses <1> to <27>,
wherein a plurality (preferably 4 or more and 20 or less) of the bonding portions 3 are preferably provided in a pair between which one of the laterally long projections 41 is provided in the longitudinal direction X.
<29>
The absorbent article as set forth in any one of clauses <1> to <28>,
wherein positions Pa and Pb of end portions Ea and Eb in the longitudinal direction X of the long bonding portion 31 and the short bonding portion 32 respectively in the longitudinal direction long bonding portion row S3 and the longitudinal direction short bonding portion row S4 that are adjacent in the width direction Y match.
<30>
The absorbent article as set forth in any one of clauses <1> to <29>,
wherein portions in the longitudinal direction X of the long bonding portion 31 and the short bonding portion 32 respectively in the longitudinal direction long bonding portion row S3 and the longitudinal direction short bonding portion row S4 that are adjacent in the width direction Y overlap.
<31>
The absorbent article as set forth in any one of clauses <1> to <30>,
wherein the longitudinal direction short bonding portion rows S4 are formed between the longitudinal direction long bonding portion rows S3 that are adjacent in the width direction Y, end portions Ea and Eb of the long bonding portion 31 in one of the longitudinal direction long bonding portion rows S3 respectively overlap portions (preferably near end portions) Ea and Eb in the longitudinal direction of the short bonding portions 32 in the longitudinal direction short bonding portion row S4 that is adjacent to the longitudinal direction long bonding portion row S3, and end portions Ec and Ed of the long bonding portion 31 in the other longitudinal direction long bonding portion row S3 respectively overlap portions (preferably near end portions) Ec and Ed in the longitudinal direction of the short bonding portions 32 in the longitudinal direction short bonding portion row S4 that is adjacent to the other longitudinal direction long bonding portion row S3.
<32>
The absorbent article as set forth in any one of clauses <1> to <31>,
wherein when a plurality of the longitudinal direction short bonding portion rows S4 are provided between the longitudinal direction long bonding portion rows S3, a distance between the short bonding portions 32 in the longitudinal direction is different between the plurality of the longitudinal direction short bonding portion rows S4.
<33>
The absorbent article as set forth in any one of clauses <1> to <32>,
wherein the laterally long projections 41 that are adjacent in the width direction Y share the long bonding portion 31 provided therebetween, and
the laterally long projections 41 that are adjacent in the first direction D1 or the second direction D2 share four out of twelve bonding portions that surround each of the laterally long projections 41.
<34>
The absorbent article as set forth in any one of clauses <1> to <33>,
wherein the laterally long projections 41 that are adjacent in the longitudinal direction projection row R3 share one of the long bonding portions 31.
<35>
The absorbent article as set forth in any one of clauses <1> to <34>,
wherein an arrangement and form of the projections are different between the central region M and the pair of side regions S and S.
<36>
The absorbent article as set forth in any one of clauses <1> to <35>,
wherein the composite sheet includes: a central region in which the laterally long projections and the bonding portions that surround the laterally long projections are formed; and a pair of side regions provided on two opposing sides of the central region, and
in each of the side regions, projections that have a length in the width direction that is shorter than a length in the width direction of the laterally long projections of the central region are formed in a staggered arrangement.
<37>
The absorbent article as set forth in any one of clauses <1> to <36>,
wherein the projections 43 formed in the side regions S have a height H3 (see FIG. 6(c)) of preferably 0.3 mm or more, more preferably 0.6 mm or more, and preferably 4.0 mm or less, more preferably 3.0 mm or less.
<38>
The absorbent article as set forth in any one of clauses <1> to <37>,
wherein, in each of the side regions S of the composite sheet 10, bonding portion pairs 34, each including a pair of the bonding portions 35 and 35 that are closely disposed at the same spacing as a spacing a2 between the longitudinal direction short bonding portion rows S4 of the central region M, are formed such that a plurality of width direction composite rows J2 in each of which the projections 43 and the bonding portion pairs 34 are alternately disposed in the width direction Y at a regular interval, and a plurality of longitudinal direction composite rows J1 in each of which the projections 43 and the bonding portion pairs 34 are alternately disposed in the longitudinal direction X at a regular interval are formed.

<39>

The absorbent article as set forth in any one of clauses <1> to <38>, wherein a non-woven fabric that is used as a sheet material that constitutes each f the first sheet and the second sheet has a basis weight of preferably 10 g/m2 or more, more preferably 15 g/m2 or more, and preferably 40 g/m2 or less, more preferably 35 g/m2 or less.

INDUSTRIAL APPLICABILITY

With the absorbent article according to the present invention, it is possible to reduce the friction on the skin due to the projections of the composite sheet that constitutes the topsheet, and also effectively prevent a problem such as side leakage caused by a liquid excessively spreading in the width direction.

The invention claimed is:

1. An absorbent article comprising:
a topsheet that comprises a composite sheet;
a backsheet; and
an absorbent member that is provided between the topsheet and the backsheet,
the absorbent article having a longitudinal direction that corresponds to a front-back direction of a wearer, and a width direction that is perpendicular to the longitudinal direction,
wherein the composite sheet includes a first sheet and a second sheet that are stacked, the first sheet and the second sheet are bonded to each other at a plurality of bonding portions, and projections that protrude toward a skin of the wearer are formed by the first sheet protruding in a direction away from the second sheet at portions other than the bonding portions,
a plurality of first oblique bonding portion rows in each of which the plurality of bonding portions are aligned in a first direction that is oblique to both the longitudinal direction and the width direction, and a plurality of second oblique bonding portion rows in each of which the plurality of bonding portions are aligned in a second direction that is oblique to both the longitudinal direction and the width direction and that intersects the first direction are formed,
a long bonding portion that is elongated in the longitudinal direction is formed at each intersection of the first oblique bonding portion rows and the second oblique bonding portion rows,
as the projections, laterally long projections that are elongated in the width direction are formed in a dispersed manner in the longitudinal direction and the width direction, and
each of the laterally long projections is surrounded by two first oblique bonding portion rows and two second oblique bonding portion rows, and the long bonding portion is formed between the laterally long projections that are adjacent in the width direction.

2. The absorbent article as set forth in claim 1,
wherein a plurality of types of bonding portions that have different lengths in the longitudinal direction are included as the bonding portions.

3. The absorbent article as set forth in claim 1,
wherein the first oblique bonding portion row and the second oblique bonding portion row include, between the intersections, a short bonding portion that has a length in the longitudinal direction that is shorter than a length in the longitudinal direction of the long bonding portion.

4. The absorbent article as set forth in claim 1,
wherein a plurality of longitudinal direction bonding portion rows in each of which the bonding portions are spaced apart and aligned in the longitudinal direction are formed in the width direction, and
the bonding portions in the longitudinal direction bonding portion rows that are adjacent in the width direction partially or entirely overlap in the longitudinal direction, or positions of end portions of the bonding portions match in the longitudinal direction.

5. The absorbent article as set forth in claim 1,
wherein a plurality of width direction composite rows in each of which the laterally long projections and the long bonding portions are disposed alternately in the width direction are formed in the longitudinal direction, and
positions of the long bonding portions in the width direction composite rows that are adjacent in the longitudinal direction are displaced by a half-pitch in the width direction.

6. The absorbent article as set forth in claim 1,
wherein the composite sheet is configured such that the laterally long projections that are adjacent in a plane direction share one or more of the bonding portions that surround each of the laterally long projections.

7. The absorbent article as set forth in claim 1,
wherein the first oblique bonding portion row and the second oblique bonding portion row have a plurality of the intersections at a regular interval in each of the first direction and the second direction, and
the long bonding portions are disposed at the intersections.

8. The absorbent article as set forth in claim 1,
wherein the first direction and the second direction are line-symmetric with respect to a symmetry line that is a straight line parallel to a longitudinal center line that extends in the longitudinal direction of the absorbent article.

9. The absorbent article as set forth in claim 1,
wherein the laterally long projections are disposed so as to form: a longitudinal direction projection row in which a plurality of the laterally long projections are aligned at a regular interval in the longitudinal direction; a width direction projection row in which a plurality of the laterally long projections are aligned at a regular interval in the width direction; a first direction projection row in which a plurality of the laterally long projections are aligned at a regular interval in the first direction; and a second direction projection row in which a plurality of the laterally long projections are aligned at a regular interval in the second direction.

10. The absorbent article as set forth in claim 1,
wherein the laterally long projections are disposed so as to form a longitudinal direction projection row in which a plurality of the laterally long projections are aligned at a regular interval in the longitudinal direction, and a width direction projection row in which a plurality of the laterally long projections are aligned at a regular interval in the width direction, placement positions of the laterally long projections are displaced by a half-pitch in the longitudinal direction between the longitudinal direction projection rows that are adjacent in the width direction, and placement positions of the laterally long projections are displaced by a half-pitch in the width direction between the width direction projection rows that are adjacent in the longitudinal direction.

11. The absorbent article as set forth in claim 1,
wherein the composite sheet is configured such that the first oblique bonding portion row and the second oblique bonding portion row include, between the intersections, a short bonding portion that has a length in the longitudinal direction that is shorter than a length in the longitudinal direction of the long bonding portion, a longitudinal direction long bonding portion row, in which a plurality of the long bonding portions are aligned at a regular interval in the longitudinal direction, and a longitudinal direction short bonding portion row, in which a plurality of the short bonding portions are aligned at a regular interval in the longitudinal direction, are included, and when two or more of the longitudinal direction short bonding portion rows are provided between the longitudinal direction long bonding portion rows, a spacing between the longitudinal direction short bonding portion row and the longitudinal direction long bonding portion row that are adjacent in the width direction is equal to a spacing between the longitudinal direction short bonding portion rows.

12. The absorbent article as set forth in claim 1,
wherein the composite sheet is configured such that the first oblique bonding portion row and the second oblique bonding portion row include, between the intersections, a short bonding portion that has a length in the longitudinal direction that is shorter than a length in the longitudinal direction of the long bonding portion, longitudinal direction long bonding portion rows, in each of which a plurality of the long bonding portions are aligned at a regular interval in the longitudinal direction, and longitudinal direction short bonding portion rows, in each of which a plurality of the short bonding portions are aligned at a regular interval in the longitudinal direction, are included, and in the longitudinal direction short bonding portion row provided between the longitudinal direction long bonding portion rows, a center position of the short bonding portion in the longitudinal direction is located between a first end of the long bonding portion of one of the longitudinal direction long bonding portion rows and a second end of the long bonding portion of the other longitudinal direction long bonding portion row.

13. The absorbent article as set forth in claim 1,
wherein the first oblique bonding portion row and the second oblique bonding portion row include, between the intersections, a short bonding portion that has a length in the longitudinal direction that is shorter than a length in the longitudinal direction of the long bonding portion, each of the laterally long projections is formed within a region surrounded by four long bonding portions that are provided at the intersections of the first oblique bonding portion row and the second oblique bonding portion row and four or more short bonding portions that are provided between the four long bonding portions.

14. The absorbent article as set forth in claim 1,
wherein each of the laterally long projections is configured such that the long bonding portion that is elongated in the longitudinal direction is formed between the laterally long projections that are adjacent in the width direction.

15. The absorbent article as set forth in claim 1,
wherein the composite sheet includes:
a width direction composite row in which the laterally long projections and the long bonding portions are alternately disposed in the width direction; and
a longitudinal direction long bonding portion row in which a plurality of the long bonding portions are aligned at a regular interval in the longitudinal direction, a length in the width direction of the laterally long projections is a distance between the long bonding portions in the width direction composite row, and a length in the longitudinal direction of the laterally long projections is the same as a distance between the long bonding portions in the longitudinal direction long bonding portion row.

16. The absorbent article as set forth in claim 1,
wherein the first oblique bonding portion row and the second oblique bonding portion row include, between the intersections, a short bonding portion that has a length in the longitudinal direction that is shorter than a length in the longitudinal direction of the long bonding portion, and the short bonding portions have a length in the longitudinal direction and a length in the width direction that are substantially the same.

17. The absorbent article as set forth in claim 1,
wherein the composite sheet is configured such that the first oblique bonding portion row and the second oblique bonding portion row include, between the intersections, a short bonding portion that has a length in the longitudinal direction that is shorter than a length in the longitudinal direction of the long bonding portion, longitudinal direction long bonding portion rows, in each of which a plurality of the long bonding portions are aligned at a regular interval in the longitudinal direction, and longitudinal direction short bonding portion rows, in each of which a plurality of the short bonding portions are aligned at a regular interval in the longitudinal direction, are included, and positions of end portions in the longitudinal direction of the long bonding portion and the short bonding portion respectively in the longitudinal direction long bonding portion row and the longitudinal direction short bonding portion row that are adjacent in the width direction match.

18. The absorbent article as set forth in claim 1,
wherein the composite sheet is configured such that the first oblique bonding portion row and the second oblique bonding portion row include, between the intersections, a short bonding portion that has a length in the longitudinal direction that is shorter than a length in the longitudinal direction of the long bonding portion, longitudinal direction long bonding portion rows, in each of which a plurality of the long bonding portions are aligned at a regular interval in the longitudinal direction, and longitudinal direction short bonding portion rows, in each of which a plurality of the short bonding portions are aligned at a regular interval in the longitudinal direction, are included, and portions in the longitudinal direction of the long bonding portion and the short bonding portion respectively in the longitudinal direction long bonding portion row and the longitudinal direction short bonding portion row that are adjacent in the width direction overlap.

19. The absorbent article as set forth in claim 1, wherein the composite sheet is configured such that the first oblique bonding portion row and the second oblique bonding portion row include, between the intersections, short bonding portions that have a length in the longitudinal direction that is shorter than a length in the longitudinal direction of the long bonding portion, longitudinal direction long bonding portion rows, in each of which a plurality of the long bonding portions are aligned at a regular interval in the longitudinal direction, and longitudinal direction short bonding portion rows, in each of which a plurality of the short bonding portions are aligned at a regular interval in the longitudinal direction, are included, and the longitudinal direction short bonding portion rows are formed between the longitudinal direction long bonding portion rows that are adjacent in the width direction, end portions of the long bonding portion in one of the longitudinal direction long bonding portion rows respectively overlap portions in the longitudinal direction of the short bonding portions in the longitudinal direction short bonding portion row that is adjacent to the longitudinal direction long bonding portion row, and end portions of the long bonding portion in the other longitudinal direction long bonding portion row respectively overlap portions in the longitudinal direction of the short bonding portions in the longitudinal direction short bonding portion row that is adjacent to the other longitudinal direction long bonding portion row.

20. The absorbent article as set forth in claim 1, wherein the composite sheet is configured such that the first oblique bonding portion row and the second oblique bonding portion row include, between the intersections, a short bonding portion that has a length in the longitudinal direction that is shorter than a length in the longitudinal direction of the long bonding portion, a longitudinal direction long bonding portion row, in which a plurality of the long bonding portions are aligned at a regular interval in the longitudinal direction, and a longitudinal direction short bonding portion row, in which a plurality of the short bonding portions are aligned at a regular interval in the longitudinal direction, are included, and when a plurality of the longitudinal direction short bonding portion rows are provided between the longitudinal direction long bonding portion rows, each distance between the short bonding portions in the longitudinal direction is different between the plurality of the longitudinal direction short bonding portion rows.

* * * * *